United States Patent [19]
Podszun et al.

[11] Patent Number: 5,808,104
[45] Date of Patent: Sep. 15, 1998

[54] POLYMERIZABLE AROMATIC CARBOXYLIC ACIDS AND CARBOXYLIC ACID ANHYDRIDES WITH CYCLIC CARBONATE GROUPS AND FORMULATIONS THEREOF

[75] Inventors: Wolfgang Podszun, Köln; Ludger Heiliger, Leverkusen; Werner Finger, Neuss; Martin Grunwald, Pulheim; Carl Casser, Köln, all of Germany

[73] Assignee: Heraeus Kulzer GmbH, Hanau, Germany

[21] Appl. No.: 899,227

[22] Filed: Jul. 23, 1997

Related U.S. Application Data

[63] Continuation of Ser. No. 813,845, filed as PCT/EP96/02987, Jul. 10, 1995, abandoned.

[30] Foreign Application Priority Data

Jul. 10, 1995 [DE] Germany ................ 195 25 033.8

[51] Int. Cl.$^6$ ............ C07D 317/36; C07D 407/10; C09J 4/02; A61K 6/02
[52] U.S. Cl. ............ 549/229; 523/120; 623/16
[58] Field of Search ............ 549/229; 523/120; 623/16

[56] References Cited

U.S. PATENT DOCUMENTS

| | | | |
|---|---|---|---|
| 4,148,988 | 4/1979 | Masuhara et al. | 526/318 |
| 4,323,696 | 4/1982 | Schmitz-Josten et al. | 560/220 |
| 4,437,836 | 3/1984 | Schmitz-Josten et al. | 433/199 |
| 4,879,402 | 11/1989 | Reiners et al. | 560/26 |
| 4,952,614 | 8/1990 | Reiners et al. | 523/115 |
| 5,241,081 | 8/1993 | Müller et al. | 549/232 |
| 5,294,646 | 3/1994 | Müller et al. | 523/120 |

FOREIGN PATENT DOCUMENTS

| | | |
|---|---|---|
| 023 686 | 2/1981 | European Pat. Off. . |
| 254 950 | 2/1988 | European Pat. Off. . |
| 471 252 A1 | 2/1992 | European Pat. Off. . |
| 471 252 B1 | 2/1992 | European Pat. Off. . |
| 31 35 113 | 3/1983 | Germany . |
| 37 03 080 | 1/1988 | Germany . |
| 37 03 120 | 1/1988 | Germany . |
| 37 03 130 | 1/1988 | Germany . |
| 43 24 614 | 1/1995 | Germany . |

OTHER PUBLICATIONS

Tadao Fukushima, Minoru Kawaguchi, Yusuke Inoue, Koji Miyazaki and Takashi Horibe, "Application of Functional Monomers for Dental Use (Part 9) Syntheses of Succinoxy Methacrylates and Their Adhesion to Polished and Etched Tooth Surfaces", *Dental Materials Journal*, 4(1), 33–39, 1985.

*Primary Examiner*—Bernard Dentz
*Attorney, Agent, or Firm*—Frishauf, Holtz, Goodman, Langer & Chick, P.C.

[57] ABSTRACT

Polymerizable aromatic carboxylic acids and carboxylic acid anhydrides with cyclic carbonate groups which are useful for improving adhesion of synthetic dental filling materials.

23 Claims, No Drawings

POLYMERIZABLE AROMATIC CARBOXYLIC ACIDS AND CARBOXYLIC ACID ANHYDRIDES WITH CYCLIC CARBONATE GROUPS AND FORMULATIONS THEREOF

CROSS REFERENCE TO RELATED APPLICATION

This application is a Continuation-in-Part application of application Ser. No. 08/813,845, filed Mar. 7, 1997 now abandoned, which is a Continuation Application of International Application PCT/EP96/02987 filed Jul. 8, 1996, the entire contents of which are incorporated by reference herein.

BACKGROUND OF THE INVENTION

1. Field of the Invention

The invention relates to new polymerizable aromatic carboxylic acids and carboxylic acid anhydrides with cyclic carbonate groups, as well as formulations of these compounds, preferably for use in dental technology.

2. Background Information

A specific serious problem in the field of conservative dentistry is to form a durable, gap-free bond of synthetic filling materials with the hard substance of the tooth (dentine and enamel). In the dental field, curable materials are used as filling materials for dental restoration. As curable materials, acrylic resin-based filling materials, which can be cured by radical polymerization, are generally preferred. A disadvantage of these materials is that they shrink during the curing process and thus contribute to the formation of gaps. Synthetic fillings have the additional disadvantage that their adhesion to dentine is poor.

In order to improve bonding with the hard substance of the tooth, so-called adhesives or adhesion promoters can be used. As an active component of such adhesives for fillings in the dental field, methacryloyloxyalkyl derivatives of aromatic carboxylic acids are used, for example. Thus, in U.S. Pat. No. 4,148,988, for example, mixtures of trimellitic acid-4-methacryloyloxyethyl ester (4-MET) or trimellitic acid anhydride-4-methacryloyloxyethyl ester (4-META) with ethylenically unsaturated monomers and polymerization initiators are described.

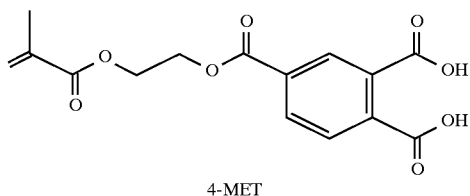

4-MET

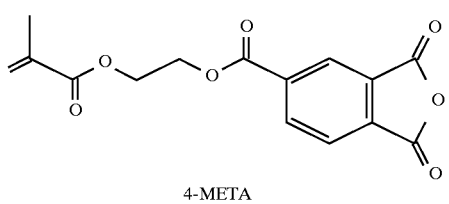

4-META

A commercial product synthesized from 4-META (Superbond from Sun Medical Co. Ltd., Moriyama, Shiga, Japan) must be mixed with methyl methacrylate (MMA), polymethyl methacrylate (PMMA) and partially oxidized tri-n-butylborane (TBB) in order to obtain the ready-to-apply form (MMA-4-META-TBB resin).

In EP 0 471 252 B1, N-alkyl-N-(meth)acryloyloxyalkylcarboxamides of aromatic carboxylic acids and carboxylic acid anhydrides are proposed as components for adhesives. Significantly simplified application formulas result for these (meth)acryloyloxyalkyl derivatives.

A disadvantage of the known (meth)acryloyloxyalkyl derivatives of aromatic carboxylic acids is their relatively poor polymerizability. This results in several serious disadvantages. For example, the curing might be incomplete which may result in monomer residues and requires using drastic conditions when curing, for example, prolonged irradiation.

SUMMARY OF THE INVENTION

It has now been discovered that with the aid of the new polymerizable aromatic carboxylic acids and carboxylic acid anhydrides with cyclic carbonate groups adhesives can be formulated, preferably such which are suitable for treating the hard substance of a tooth, which provides a significantly enhanced polymerizability.

The new compounds correspond to the formula (I)

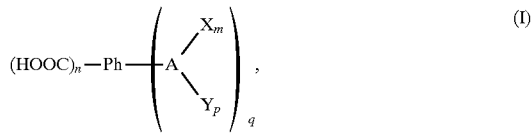

in which

Ph stands for a tri- or tetrasubstituted benzene ring (1,2,3-/1,2,4- or 1,2,4,5-substitution) or a tri- or tetra-substituted naphthalene ring (1,2,6-/1,4,5-/2,3,6-/1,4,5, 8- or 2,3,6,7-substitution), wherein the substituents for Ph are the $(HOOC)_n$ and the $(A(Xm) (Yp))_q$ groups, A refers to a (m+p+1)-valent aliphatic residue with 3 to 15 C-atoms which may be substituted with OH groups and may contain up to 5 ether bridges, X refers to a methacrylate or acrylate group, Y refers to

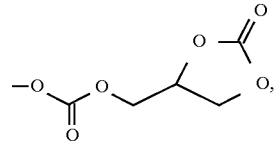

n refers to 2 or 3,
m refers to 1, 2, 3 or 4,
p refers to 1, 2, 3 or 4,
q refers to 1 or 2.

DETAILED DESCRIPTION OF THE INVENTION

The aliphatic residue A in formula (I) may be linear, branched or cyclic. Particularly preferred are linear or branched residues. Particularly well-suited aliphatic residues A are, for example, selected from the group consisting of

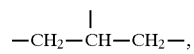

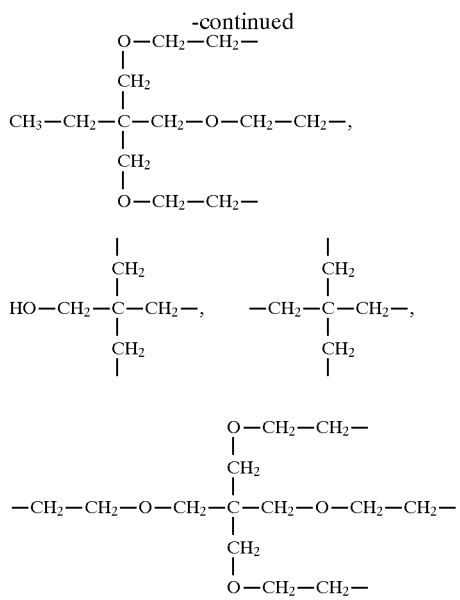

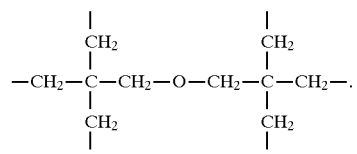

and

-CH₂-C(CH₂)(CH₂)-CH₂-O-CH₂-C(CH₂)(CH₂)-CH₂-.

Two COOH groups may also be combined to form an anhydride group, provided that both COOH groups are vicinally bound to an aromatic hydrocarbon. In this context, vicinally appropriate are ortho positions with respect to benzene and naphthalene rings and α-positions (1,8- or 4,5-substitution, respectively) with respect to naphthalene rings.

Ph refers to a benzene ring trisubstituted in the 1,2,3- or 1,2,4-position, respectively, or tetrasubstituted in the 1,2,4,5-position, or a naphthalene ring trisubstituted in the 1,2,6-,1,4,5-or 2,3,6-position, respectively, or tetrasubstituted in the 2,3,6,7- or 1,4,5,8-position, respectively.

Non-limiting examples of the polymerizable aromatic carboxylic acids and carboxylic acid anhydrides with cyclic carbonate groups according to the present invention are set forth in the following Table 1.

TABLE 1

Carboxylic Acids and Carboxylic Acid Anhydrides According to the Present Invention

| No. | Formula | No. | Formula |
|---|---|---|---|
| 1 | (structure) | 2 | (structure) |
| 3 | (structure) | 4 | (structure) |
| 5 | (structure) | 6 | (structure) |

TABLE 1-continued

Carboxylic Acids and Carboxylic Acid Anhydrides According to the Present Invention

| No. | Formula | No. | Formula |
|-----|---------|-----|---------|
| 7 | (structure) | 8 | (structure) |
| 9 | (structure) | 10 | (structure) |

TABLE 1-continued

Carboxylic Acids and Carboxylic Acid Anhydrides According to the Present Invention The preparation of the polymerizable aromatic carboxylic acids and carboxylic acid anhydrides according to the present invention suitably takes place through reaction of aromatic monoanhydrides or dianhydrides with multifunctional hydroxyalkyl(meth)acrylates corresponding to the following formula (II):

(II)

wherein A, X, Y, m and p have the above described meanings.

As monoanhydrides, the commercially available trimellitic acid derivatives 1,2,4-benzene-tricarboxylic acid anhydride chloride and 1,2,4-benzene-tricarboxylic acid anhydride, the hemimellitic acid derivatives known from the literature 1,2,3-benzene-tricarboxylic acid anhydride and 1,2,3-benzene-tricarboxylic acid anhydride chloride, and the naphthalene-tricarboxylic acid derivatives 1,2,6-and 1,4,5-naphthalene-tricarboxylic acid anhydride chloride, are preferred.

As dianhydrides, the commercially available compounds benzene-1,2,4,5-tetracarboxylic acid dianhydride (pyromellitic dianhydride), naphthalene-1,4,5,8-tetracarboxylic acid dianhydride and naphthalene-2,3,6,7-tetracarboxylic acid dianhydride, which forms simply through dehydration of the known naphthalene-2,3,6,7-tetracarboxylic acid, are preferred.

The hydroxyalkyl(meth)acrylates with the formula (II)

(II)

which form the basis of the polymerizable aromatic carboxylic acids and carboxylic acid anhydrides are available through gradual esterification of polyhydroxyalkyl compounds with, for example, (meth)acrylic acid chloride and the chloroformic acid ester corresponding to the following formula (III):

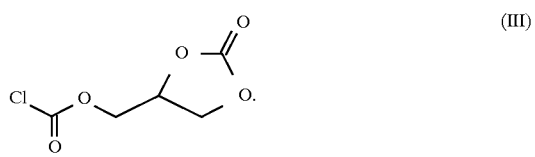
(III)

The chloroformic acid ester according to formula (III) can be prepared by phosgenation of glycerol. This synthesis step is described in detail in U.S. Pat. No. 2,446,145.

The preparation of the polymerizable aromatic carboxylic acids and carboxylic acid anhydrides according to the present invention preferably takes place in an organic solvent. Suitable organic solvents are aprotic solvents such as dioxane, tetrahydrofuran, N,N-dimethyl formamide, N,N-dimethyl acetamide, dimethyl sulphonamide and acetone. More suitable are toluene and diethyl ether. Particularly preferred are xylene, dichloromethane, chloroform and methyltert.-butyl ether.

A suitable temperature range for the preparation of the polymerizable aromatic carboxylic acids and carboxylic acid anhydrides according to the present invention is between −30° and 110° C. It is preferred that the reaction be carried out between −10° and 50° C. and particularly preferred between −5° and 30° C. Additionally, inorganic or organic bases can be used for the preparation.

Preferred inorganic bases are the weak alkaline carbonates and hydrogencarbonates of sodium and potassium. Preferred organic bases are tert. amines, whereby triethylamine and pyridine are particularly preferred. The bases are used, with respect to the anhydride, in an equimolar up to a quinquemolar quantity, whereby a dimolar to trimolar excess is preferred. The organic bases additionally act as a solubilizer.

For the preparation of the polymerizable aromatic carboxylic acids with vicinal carboxylic acid groups, first the corresponding anhydrides can be synthesized. From the anhydrides, the dicarboxylic acids are available by means of hydrolysis at temperatures ranging between 5° and 100° C., preferably 20° and 50° C. The hydrolysis can take place subsequent to isolation of the anhydrides. A direct hydrolysis of the reaction batch is, however, also possible. To perform the hydrolysis, water is added in an equimolar quantity, preferred, however, is in excess of a decamolar quantity. The hydrolysis can be catalyzed through the targeted addition of acids, especially sulfuric acid, phosphoric acid, toluenesulphonic acid or acid ion exchangers, or through the addition of bases, such as sodium and potassium hydroxide, sodium and potassium carbonate or sodium and potassium hydrogencarbonate.

The reactivity of compounds curable through polymerization can be precisely described through the photo-DSC method (Differential Scanning Calorimetry).

In this method, photoactivated samples are irradiated in a DSC apparatus with a high-intensity irradiation source, for example, a halogen lamp with heat protection filter. The heat flow is recorded under irradiation as a function of time. As a reference, samples with the same composition without a photo-initiator are used. As a measurement of the reaction rate, the t-max value is determined. t-max is the time from initiation of the irradiation to obtaining of the reaction maximum (maximum heat flow); the smaller the t-max, the greater the photo-reactivity.

The formulations according to the present invention contain, aside from the new polymerizable aromatic carboxylic acids and carboxylic acid anhydrides (I), solvents, initiators, co-activators and, optionally, additional (meth) acrylic acid esters as co-monomers. Mixtures of various polymerizable aromatic carboxylic acids and carboxylic acid anhydrides (I) according to the present invention can also be used in the formulations according to the present invention.

The solvents of the formulations must dissolve the components and, if the formulation is for dental purposes, must be non-toxic. Preferred are water and volatile organic solvents such as methanol, ethanol, propyl alcohol, isopropyl alcohol, acetone, methyl ethyl ketone, methyl acetate and ethyl acetate and tetrahydrofuran. Generally, one uses 10 to 1000 parts by weight, preferably 50 to 300 parts by weight, of the solvent, with respect to the polymerizable aromatic carboxylic acids and carboxylic acid anhydrides (I). Mixtures of these solvents can also be particularly preferred, whereby aqueous mixtures are especially preferred.

Initiators within the framework of the present invention include radical formers which initiate a radical polymerization. Preferred are photo-initiators which initiate a radical polymerization when exposed to light, for example, UV light, visible light or laser light.

These so-called photo-polymerization initiators are generally known from the literature. Preferably, they are mono- or dicarbonyl compounds such as benzophenone, benzoin and its derivatives, in particular benzoin methyl ether, benzil and benzil derivatives, and other dicarbonyl compounds, such as diacetyl, 2,3-pentanedione and α-diketo derivatives of norbornane and substituted norbornanes, metal carbonyls, such as pentacarbonyl manganese, or quinones, such as 9,10-phenanthrenequinone and naphthoquinone. Especially preferred is camphorquinone.

The formulations according to the present invention generally contain 0.01 to 2% by weight, preferably 0.1 to 0.5% by weight, of an initiator, with respect to the quantity of polymerizable compounds.

If one of the compound components in contact with the formulation according to the present invention already contains an initiator of the described type, one may omit the initiator in the formulation.

It can be advantageous to add co-activators to the formulations according to the present invention, which accelerate the polymerization reaction. Known accelerators are, for example, amines, such as p-toluidine, dimethyl-p-toluidine, trialkylamines, such as trihexylamine, polyamines, such as N,N,N',N'-tetraalkylenediamines, barbituric acid and dialkyl barbituric acids. Dimethylamino benzene-sulphonamides as described in DE-A 31 35 113 are particularly preferred.

Co-activators are generally used in a quantity of 0.02 to 4% by weight, preferred is 0.2 to 1% by weight, with respect to the quantity of polymerizable compounds.

Other suitable components for the formulations according to the invention are (meth)acrylic esters as co-monomers. Preferred are esters of (meth)acrylic acid with mono- to pentahydric alcohols with 2 to 30 carbon atoms. Epoxide (meth)acrylates and urethane (meth)acrylates are particularly preferred.

Also found useful are tricyclodecane derivatives (EP-A 0 023 686) and reaction products from polyols, diisocyanates and hydroxyalkyl methacrylates (DE-A 37 03 120, DE-A 37 03 080 and DE-A 37 03 130).

Particularly preferred as the (meth)acrylic acid ester as a comonomer is the so-called Bis-GMA having the following formula:

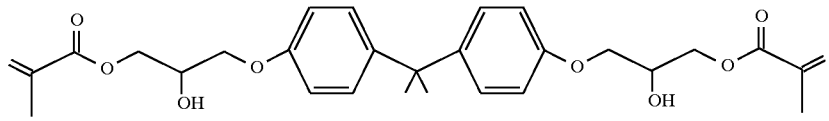

Of course, it is possible to use mixtures of the various (meth)acrylic acid esters, for example, mixtures of 20 to 70 parts by weight of Bis-GMA and 30 to 80 parts by weight of triethylene glycol di(meth)acrylate.

Furthermore, the formulations according to the present invention can contain up to 10 parts by weight of standard additives, such as stabilizers, inhibitors and light-protective agents.

The formulations according to the present invention can be prepared by mixing, through intensive stirring, the polymerizable aromatic carboxylic acids and carboxylic acid anhydrides (I), solvent, initiator and, optionally, additional components.

The formulations according to the present invention are preferably used as adhesives, particularly for improving adhesion of polymerizable dental materials to the hard substance of the tooth-enamel and collagen-containing dentine.

In a special embodiment, prior to treatment with the formulations according to the present invention, the collagen-containing hard substance of a tooth is conditioned with a fluid which has a pH value in the range of 0.1 to 3.5. This conditioning fluid generally contains acids with a $pK_a$ value less than 5 and, optionally, an amphoteric amino compound with a $pK_a$ value in the range of 9.0 to 10.6 and a $pK_b$ value in the range of 11.5 to 12.5. The following acids, for example, can be contained in the conditioning fluid: phosphoric acid, nitric acid, pyruvic acid, citric acid, oxalic acid, ethylenediaminetetraacetic acid, acetic acid, tartaric acid, and malic acid. Furthermore, the conditioning fluid can contain substances from the group of polyethylene glycols and metal hydroxides. In particular, the above listed polybasic acids can also be used in the form of partial metallic salts, as long as free acid functions remain.

Use of the formulations according to the present invention as adhesives can, for example, be carried out as follows:

When performing dental restoration, after mechanically cleaning the collagen-containing hard substance of a tooth, one first applies the conditioning fluid with a small amount of cotton wool, allows it to act for a short period of time (for example, 60 seconds), rinses the tooth material with water and dries it with an air flow. Thereafter, one applies the formulation according to the present invention in one thin layer with, for example, a small brush, and dries it with an air flow. Subsequently, the actual filling material is applied, for example, a synthetic filling material standard in the dental field.

Aside from their use in formulations suitable as adhesives, the polymerizable aromatic carboxylic acids and carboxylic acid anhydrides of the present invention can also be used advantageously as mixing fluids for glass-ionomer cements and in bone cements.

EXAMPLES

Examples 1–3

Preparation of Polymerizable Carboxylic Acids and Carboxylic Acid Anhydrides

Example 1

Preparation of Compounds 1 and 2 from Table 1

In 500 ml dry methyl ethyl ketone 160.2 g glycerol monomethacrylate (1 mole) and 202 g (1 mole) triethylamine are dissolved. The batch is cooled to −5° C. and an influent consisting of 210.57 g trimellitic acid anhydride chloride and 180.6 g (1 mole) chloroformic acid ester corresponding to formula (III), dissolved in 400 ml dry methyl ethyl ketone, is added in drops. After the adding is completed, stirring takes place for 16 hours at 0° C. Then the resulting precipitate is cold-filtered out, the filtrate is shaken out with 0.1 n hydrochloric acid and with water, the organic phase separated off and dried over sodium sulphate.

The obtained methyl ethyl ketone solution contains the compound 2 from Table 1 and can be used directly for the hydrolysis of the remaining anhydride groups. For this, 50 ml de-ionized water is added to the solution which is then stirred at ambient temperature for a period of 16 hours. After addition of 200 mg 2,6-di-tert.-butyl cresol the obtained solution can be concentrated to 372.1 g (75% of the theoretical amount) of a yellowish viscous oil (compound 1 from Table 1).

IR:=3400, 3200, 2950, 2600, 2400, 1800, 1735, 1640, 1490, 1460, 1390, 1290, 1250, 1185, 1100, 1060, 960, 870, 787, 715 cm$^{-1}$.

$^1$H-NMR (CDCl$_3$, 200 MHz):=8.6–7.8 (3H); 6.2 and 5.7 (each 1H); 5.2 (1H); 4.8–4.3 (9H); 1.9 (3H) ppm.

Example 2

Preparation of Compounds 5 and 6 from Table 1

In 500 ml dry methyl ethyl ketone 160.2 g glycerol monomethacrylate (1 mole) and 202 g (1 mole) triethylamine are dissolved. The batch is cooled at −5° C. and an influent consisting of 327.18 g (1.5 mole) of pyromellitic dianhydride and 180.6 g (1 mole) chloroformic acid ester corresponding to formula (III), dissolved in 400 ml dry methyl ethyl ketone, is added in drops. After the adding is completed, stirring takes place for 2 hours at 0° C., followed by 14 hours at ambient temperature. Then the resulting precipitate is filtered out, the filtrate is shaken out with 0.1 n hydrochloric acid and then with water, the organic phase separated off and dried over sodium sulphate.

The obtained methyl ethyl ketone solution contains the desired compound 6 from Table 1. For hydrolysis 50 ml of de-ionized water is added to the solution which is then stirred at ambient temperature for a period of 16 hours. After addition of 200 mg of 2,6-di-tert.-butyl cresol the solution can be concentrated to 292.5 g (45% of the theoretical amount) of a yellowish viscous oil (compound 5 from Table 1).

IR:=3400, 3050, 2950, 2550, 2350, 1800, 1720, 1640, 1550, 1495, 1460, 1390, 1350, 1250, 1170, 1115, 1060, 950, 760, 695 cm$^{-1}$.

$^1$H-NMR (acetone-d$_6$, 200 MHz): 8.3–8.0 (2H); 6.1 and 5.65 (each 1H); 5.1 (1H); 4.8 (1H); 4.3–4.2 (9H); 1.9 (3H) ppm.

Example 3

Preparation of Compounds 15 and 16 from Table 1

In 500 ml dry methyl ethyl ketone 160.2 g glycerol monomethacrylate (1 mole; Polyscience, Inc.) and 202 g (1 mole) triethylamine are dissolved. The batch is cooled to −5° C. and an influent consisting of 402.27 g (1.5 mole) of naphthalene-1,4,5,8-tetracarboxylic acid dianhydride and 180.6 g (1 mole) chloroformic acid ester corresponding to formula (III), dissolved in 400 ml dry methyl ethyl ketone, is added in drops. After the adding is completed, stirring takes place for 2 hours at 0° C., followed by 14 hours at ambient temperature. Then the resulting precipitate is filtered out, the filtrate is shaken out with 0.1 n hydrochloric acid and then with water, the organic phase is separated off and dried over sodium sulphate.

The obtained methyl ethyl ketone solution contains the desired compound 15 from Table 1. For hydrolysis 50 ml of de-ionized water is added to the solution which is then stirred at ambient temperature for a period of 16 hours. After addition of 200 mg 2,6-di-tert.-butyl cresol the obtained solution can be concentrated to 253.6 g (35% of the theoretical amount) of a yellowish viscous oil Compound 0.6 from Table 1.

IR: =3400, 3050, 2925, 2500, 2300, 1940, 1800–1700, 1640, 1600, 1490, 1440, 1390, 1300, 1155, 1050, 955, 890, 820, 765, 720 cm$^{-1}$.

Example 4

Testing of the Photo-reactivity of (Meth)acryloyloxyalkyl Esters With the Aid of the Photo-DSC Method (Differential Scanning Calorimetry)

The following components were intensively mixed with each other:

5.0 g (Meth)acryloyloxyalkyl ester
10 mg Camphorquinone
25 mg p-dimethylaminobenzenesulphonic acid-N,N-diallyl amide (DASA).

Camphorquinone and p-dimethylaminobenzenesulphonic acid-N,N-diallyl amide form the photo-initiator system.

The samples were irradiated at 30° C. in a DSC apparatus with a halogen lamp (75 W) with heat protection filter. The heat flow was recorded under irradiation as a function of time. As a reference, samples with the same composition without a photo-initiator were used. During the test, rinsing with nitrogen took place. For the evaluation, the t-max value was determined as a measurement of the reaction rate. The value t-max is the time from initiation of the irradiation to obtaining of the reaction maximum (maximum heat flow); the smaller the t-max, the larger the photo-reactivity.

| (Meth)acryloyloxyalkyl ester | t-max [min] |
|---|---|
| Compound 1 from Table 1 | 0.63 |
| Compound 2 from Table 1 | 0.47 |
| 4-MET (comparison) | 1.1 |

Example 5

Inhibition of the Polymerization Through Oxygen

To test the inhibition sensitivity of monomers, the thickness of the non-polymerized surface layer of samples which were irradiated with light in accordance with Example 4 is determined.

Cylindrical molds (diameter of 6 mm, depth of 0.5 mm), which were drilled into a rectangular brass plate, are filled in three layers with the monomer to be tested and, after evaporating the solvent, irradiated with the Translux CL (Heraeus Kulzer GmbH, Hanau, Germany) light device for a duration of 20 seconds at ambient atmosphere and dusted with a very small amount of colloidal silver powder. The brass plate is then placed on the stage of a reflected-light microscope against a rectangular frame support. The stage position can be adjusted with the aid of two servo-motors in the x and y directions with a reproducibility of ±1 μm. With a constant y position, the height coordinates z are then determined at a distance of 1 mm along the x axis with the depth-of-field method. The z-value determination is carried out by means of a displacement pickup which is attached to the stage vertical to the stage plane and which indicates the height adjustment in micrometer units by means of a calibrated voltmeter. The reproducibility of the z-value determination is ±1 μm. Immediately subsequent to determination of the initial value, the sample surface is carefully washed with ethanol. The mold is then returned to the microscope stage and, after entering the x/y starting positions, the z values are again determined. The differences between the first and second measurements are recorded as a mean value per sample and correspond to the surface layer which is not polymerized due to the inhibition through oxygen. Three samples are prepared and measured per monomer.

The smaller the thickness of the non-polymerized surface layer (inhibition layer), the smaller the inhibition through oxygen, the better the curing and thus the mechanical resistance of the polymerizate and the entire system to be cemented.

Results

Non-polymerized surface layer (μm)
Compound 2 from Table 1 1.3±0.8

4-MET (comparative test) totally washable, that is, no curing.

Only the compound according to the present invention demonstrates curing with a very small inhibition layer.

Examples 6 and 7

Preparation of Formulations for Use as Adhesives

Example 6

A formulation according to the present invention for use as an adhesive is prepared by intensively mixing the following components listed in this example.

5 g Acetone 2.5 g Compound 1 from table 1

2.5 g Hydroxyethylmethacrylate 0.01 g Camphorquinone 0.025 g DASA

Example 7

For comparative purposes, a formulation containing 4-MET for use as an adhesive is prepared by intensively mixing the following:

5 g Acetone 5 g 4-MET 0.01 g Camphorquinone 0.025 g DASA.

The effectiveness of the adhesives was tested by determining the shear bonding strengths with respect to enamel and dentine and performing a microscopic edge analysis on cylindrical dentine cavities which were filled with a conventional composite filling material (Pekafill, Heraeus Kulzer GmbH, Hanau, Germany) subsequent to conditioning of the dentine and application of the adhesive. Human teeth were used which had been preserved in 1 wt. % chloramine solution for a maximum of three months after extraction. Prior to their use in the test and after a careful cleaning under running water, the teeth were stored in a physiological salt solution for a minimum of three, but a maximum of ten days.

Shear Bonding Strength

On the day before their use in the bonding test, the teeth, lying on an approximal side, are individually embedded with epoxy resin (Lekutherm® X20, curing agent T3, Bayer AG, Leverkusen Germany) in cylindrical rubber molds having a diameter of 25 mm and a height of 12 mm. The teeth are ground by means of wet-grinding with SiC papers with a coarseness of 240, 320, 400 and, finally, 600, to the extent that a sufficiently large enamel surface or a peripheral dentine surface is exposed to allow bonding to it a synthetic cylinder with a diameter of 3.5 mm. Subsequent to rinsing with deionized water and drying with an air flow, the conditioning gel Gluma CPS (20 wt. % $H_3PO_4$, Heraeus Kulzer GmbH, Hanau, Germany) is applied and carefully rinsed off with a spray of water after 30 seconds. The conditioned tooth surface is then exposed to a weak air flow for a very limited period of time only in order to remove the water from the surface (wet technique!). A thin layer of adhesive is applied with a brush and the solvent is evaporated by carefully blowing it off with compressed air. The application and evaporation is repeated twice prior to irradiation with the Translux CL light device for a duration of 20 seconds. The pretreated test sample is then clamped with a clamping device under a double-part cylindrical teflon mold (diameter of 3.5 mm, height of 1 mm). Then the filling material is applied with a syringe, the mold filled with excess is covered with a transparent strip and, finally, irradiated with the Translux CL light device for a duration of 60 seconds. Immediately afterwards, the teflon mold is removed and the test sample is stored in 37° C. warm water for a period of 24 hours until initiation of the shearing stress. For that, the cylindrical test sample is stressed in a universal testing machine with the aid of a force piece parallel and very close to the ground tooth surface, at a speed of 1 mm/minute, until the cylinder separates from the tooth. The shear bonding strength is the quotient of the breaking strength and the bonding surface and is indicated in MPa. The localization of the fracture is inspected under the stereomicroscope (magnification 60×) and described as adhesive or cohesive failure.

Results

Shear bonding strength to dentine (MPa)

Formulation according to Example 6 11.7±0.4

Formulation according to Example 7 7.2±0.9

(Comparative test)

Solely with the formulation according to the present invention from Example 6 was the fracture situated interfacially adjacent in the synthetic material (cohesive failure). The formulation from Example 7 (comparative test) exhibited adhesive failure.

Shear bonding strength to enamel (MPa)

Formulation according to Example 6 20.1±1.5

Formulation according to Example 7 8.3±2.4

(Comparative test)

Solely with the formulation according to the present invention from Example 6 was the fracture situated deep in the enamel. The formulation from Example 7 (comparative test) exhibited adhesive failure.

This confirms that only in the case of the use of the formulation according to the present invention is the bond between the substrates stronger than the cohesive strength of the synthetic material and enamel. This confirms the favorable performance of the formulations according to the invention.

Microscopic Edge Analysis

To determine the cavity edge adaptation, extracted premolars or molars are ground on their approximal side by means of wet-grinding with SiC paper with a coarseness of 600 to the extent that a sufficiently large dentine surface is exposed in which a cylindrical cavity (diameter of 3 mm, depth of approximately 1.5 mm) can be prepared. The cavity is form-finished using a medium-coarse diamond instrument with the aid of a high-speed dental angle implement under water-cooling. After careful cleaning with water, conditioning and application of the adhesive takes place as described above prior to filling in the composite material Pekafill, covering with a strip and irradiating with the Translux CL light device for a duration of 60 seconds. Immediately after polymerization, the teeth are stored in water for 10–15 minutes at ambient temperature, prior to removing the excess filling material through careful wet-grinding with SiC paper 600 and 4000 and exposing of the cavity edge. Immediately thereafter an inspection of the cavity edge is performed under a reflected-light microscope at 500-fold magnification. If a separation of the filling material has occurred, the maximum gap width is determined with the aid of a screw-type micrometer eyepiece and indicated in µm.

The microscopic inspection is performed within a maximum of five minutes before gaps can occur due to drying.

Results

The formulation according to the present invention from Example 6 turns out to be extremely effective. No gap was found, the cavity edge adaptation was perfect. The bonding to dentine took place via a hybrid layer formation which, corresponding to the preceding conditioning, has a layer thickness of 10–14 µm. In contrast, the comparison from Example 7 shows separation of the filling material with a gap of 7 µm.

Example 8

Preparation of mixing fluids for glass-ionomer cements

Mixing fluids for light-curing glass-ionomer cements were prepared by mixing the following components:

| Components | A | B | C | D |
|---|---|---|---|---|
| 1,3-glycerol dimethacrylate [%] | 40 | 35 | 35 | 45 |
| HEMA [%] (hydroxyethylmethacrylate) | 39 | 29 | 34 | 44 |
| Compound 2 from Table 1 [%] | 10 | 25 | 15 | — |
| Water [%] | 10 | 10 | 15 | 10 |
| Camphorquinone [%] | 0.45 | 0.45 | 0.45 | 0.45 |
| DASA [%] | 0.45 | 0.45 | 0.45 | 0.45 |
| Jonol (2,6-di-tert.-butyl-4-methylphenol) (stabilizer) | 0.10 | 0.10 | 0.10 | 0.10 |

Additionally, a powdery mixture was prepared made of the following:
  a) 47% glass-ionomer powder consisting of
    35.9% by weight of $SiO_2$
    22.5% by weight of $Al_2O_3$
    9% by weight of $Na_3AlF_6$
    6.6% by weight of $AlF_3$
    5% by weight of $AlPO_4$
    21% by weight of $CaF_2$,
  b) 47% of barium-containing dental glass "Type GM 27884" (Schrott Glaswerke, Mainz, Germany), $d_{50}$ approximately 1.3 µm, and
  c) 6% of Aerosil VP-R 711 (Degussa AG, Frankfurt, Germany).

Three parts of the powdery mixture are mixed with one part each of the mixing fluids A–D and irradiated with the Translux CL light device for a duration of 60 seconds.

Through the method for determining inhibition described in Example 5, the value for the thickness of the inhibition layers were determined as follows:

| Mixing fluid | Compound 2 from Table 1 [%] | Inhibition layer [µm] |
|---|---|---|
| A | 10 | 2.9 |
| B | 25 | 1.5 |
| C | 15 | 2.81 |
| D | — | 12.6 |

Only the mixing fluids with the compound according to the present invention demonstrate good light-curing coupled with a significant decrease in the thickness of the inhibition layer.

What is claimed is:

1. A polymerizable (meth)acrylic acid ester of an aromatic carboxylic acid or a carboxylic acid anhydride derivative, containing cyclic carbonate groups, which is a compound selected from the group consisting of

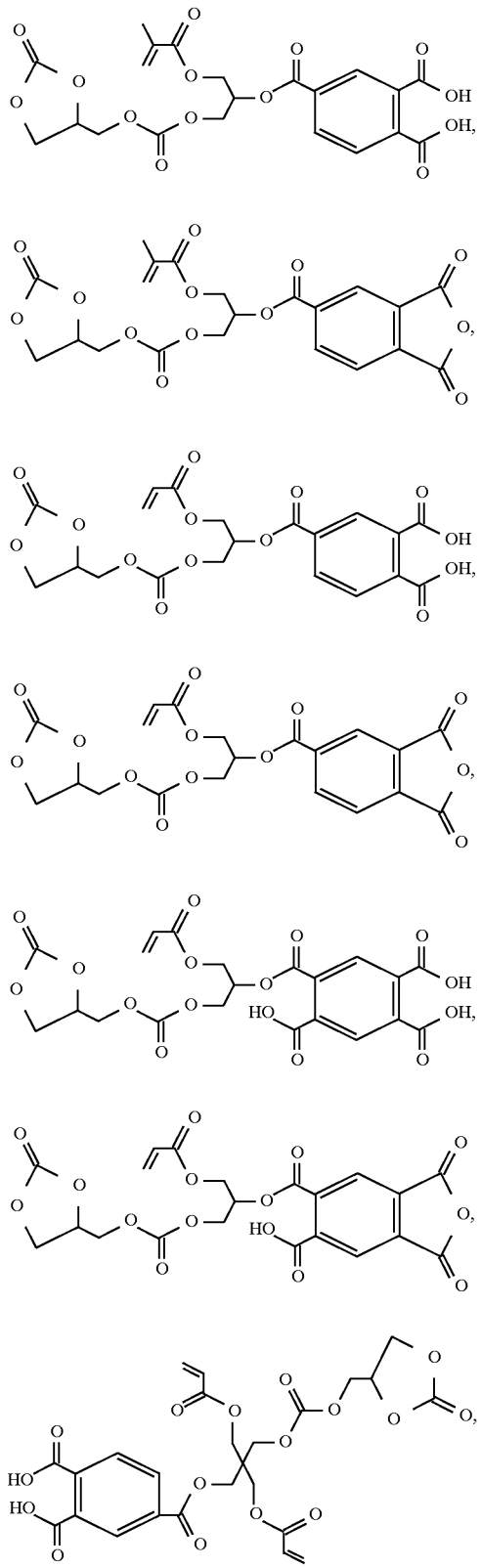

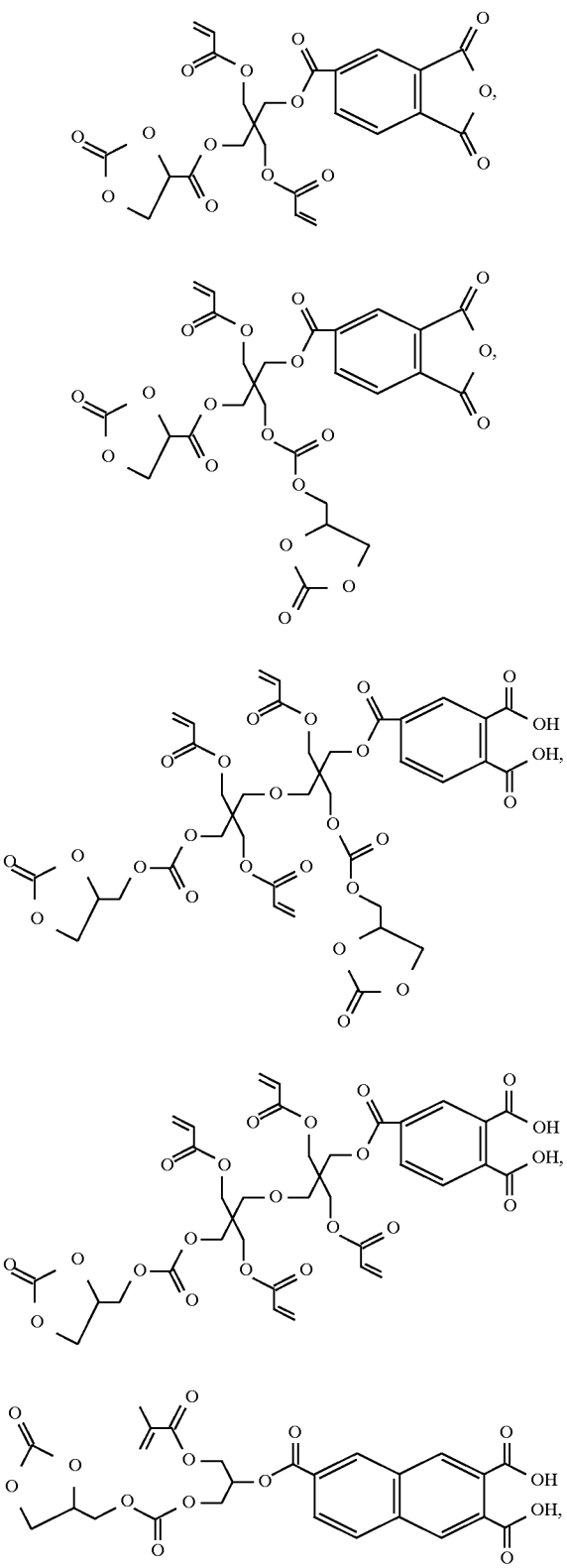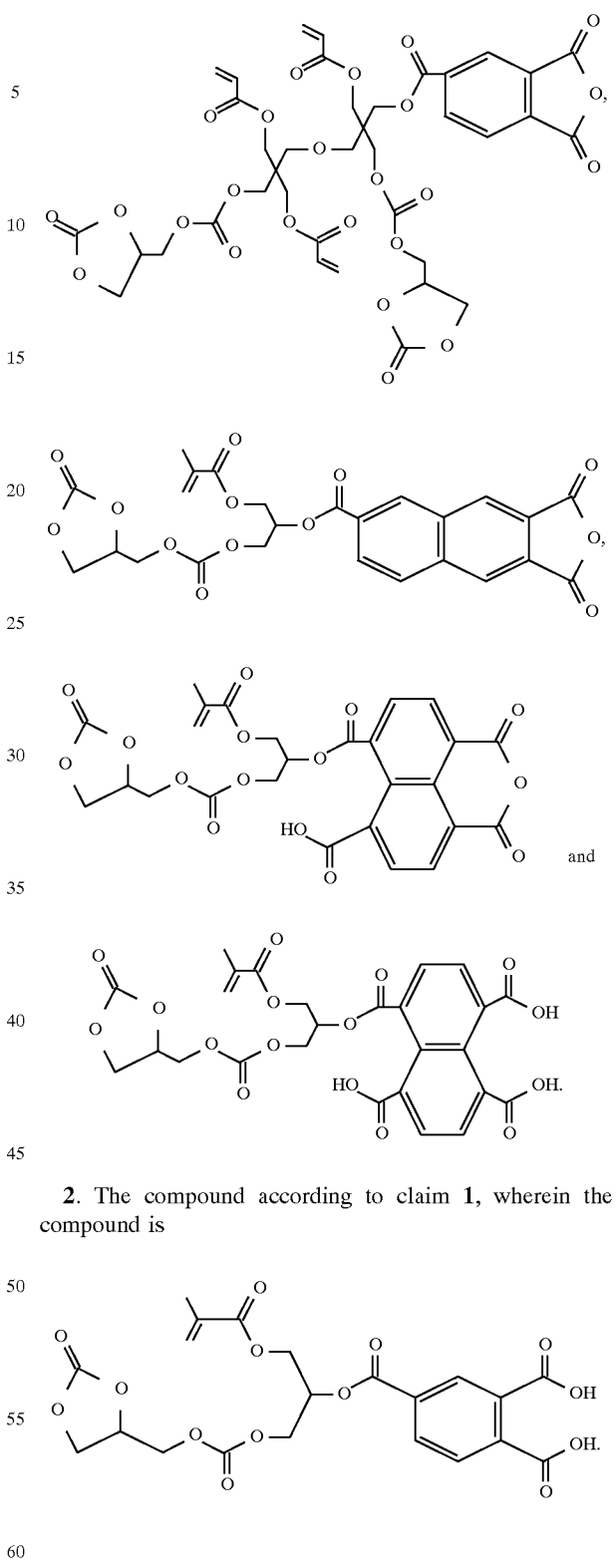
2. The compound according to claim 1, wherein the compound is 3. The compound according to claim 1, wherein the compound is

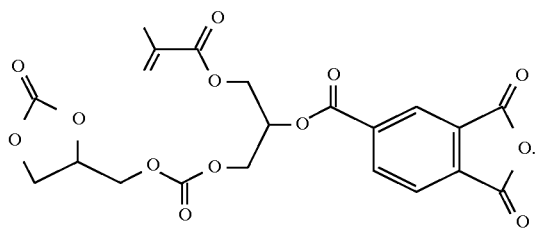

4. The compound according to claim 1, wherein the compound is

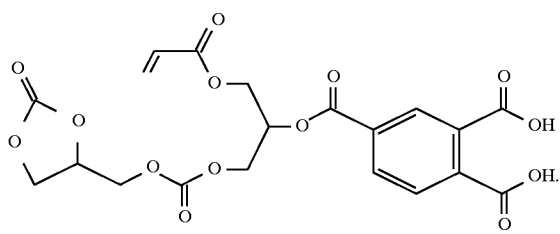

5. The compound according to claim 1, wherein the compound is

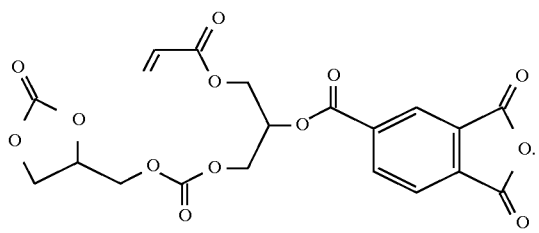

6. The compound according to claim 1, wherein the compound is

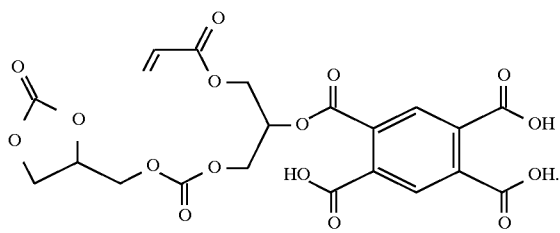

7. The compound according to claim 1, wherein the compound is

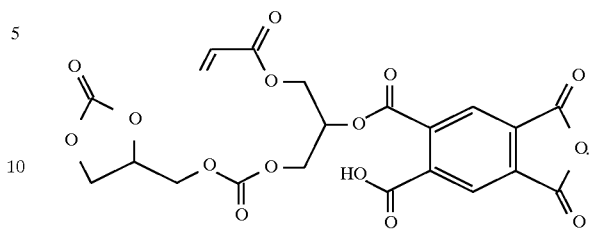

8. The compound according to claim 1, wherein the compound is

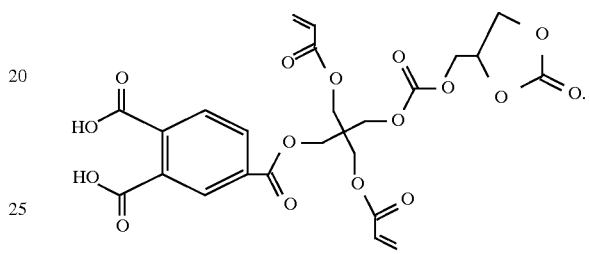

9. The compound according to claim 1, wherein the compound is

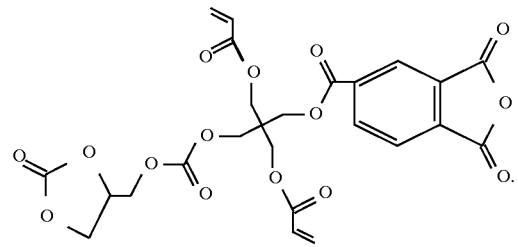

10. The compound according to claim 1, wherein the compound is

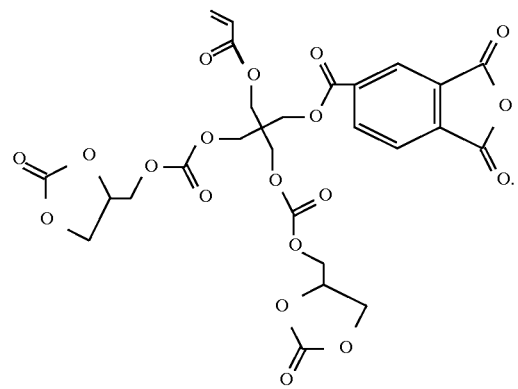

11. The compound according to claim 1, wherein the compound is
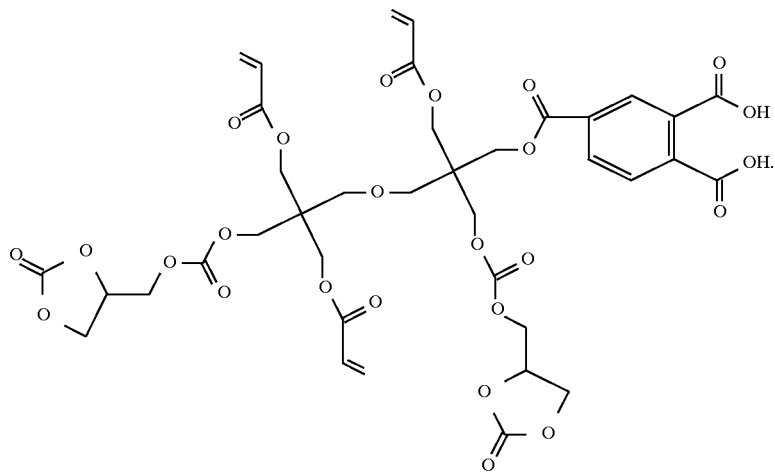
12. The compound according to claim 1, wherein the compound is
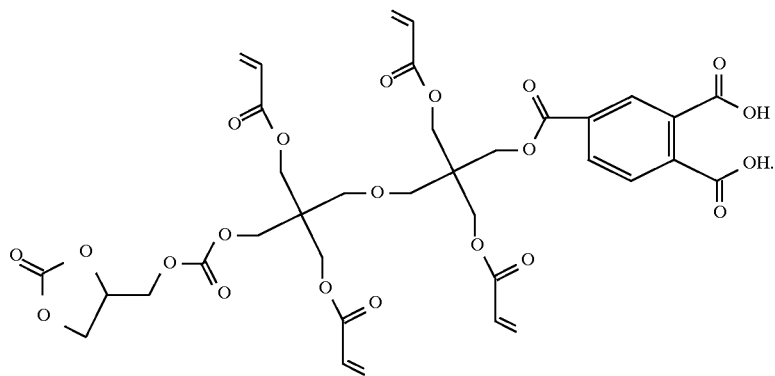
13. The compound according to claim 1, wherein the compound is
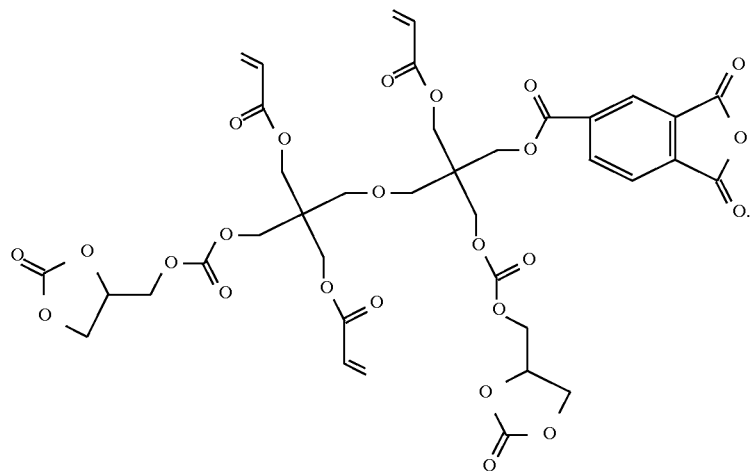

14. The compound according to claim 1, wherein the compound is

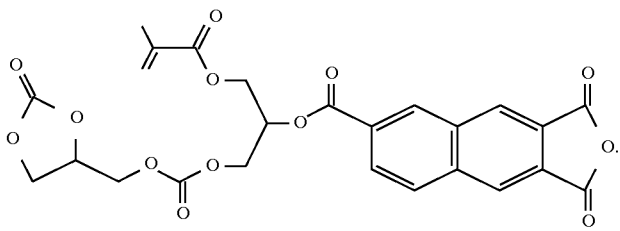

15. The compound according to claim 1, wherein the compound is

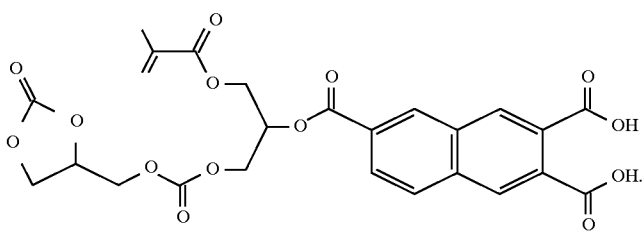

16. The compound according to claim 1, wherein the compound is

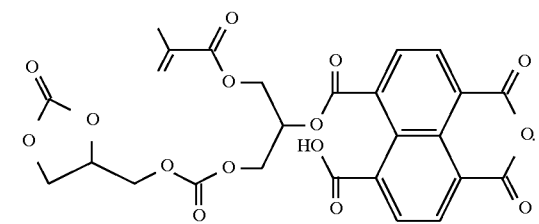

17. The compound according to claim 1, wherein the compound is

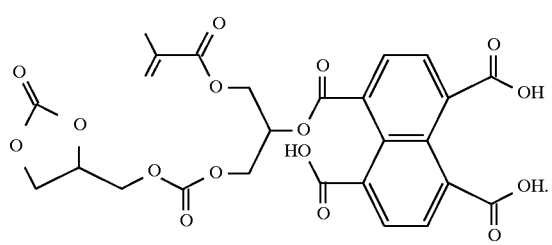

18. A formulation comprising an effective adhesive amount of the compound of claim 1 and at least one additional component selected from the group consisting of a solvent, an initiator, a co-activator, a co-monomer, a stabilizer, an inhibitor and a light-protective agent.

19. The formulation according to claim 18, which contains an initiator for initiating a radical polymerization, the initiator being a monocarbonyl compound or a dicarbonyl compound.

20. A method for improving the adhesion of a polymerizable dental filling material to the enamel or the collagen-containing dentine of a tooth, comprising contacting the tooth with an effective adhesive improving amount of a compound according to claim 1.

21. A method of improving adhesion of a polymerizable dental filling material to the collagen-containing dentine of a tooth comprising contacting a tooth with a fluid having a pH value of 0.1 to 3.5, the fluid containing at least one acid with a $PK_a$ value of less than 5 and optionally an amphoteric amino compound with a $pK_a$ value of 9.0 to 10.6 and a $pK_b$ value of 11.5 to 12.5 and then contacting the tooth with an effective adhesive improving amount of a compound according to claim 1.

22. In a mixing fluid for a glass-ionomer cement, the improvement comprising the mixing fluid containing a compound according to claim 1.

23. In a bone cement, the improvement comprising the bone cement containing a compound according to claim 1.

* * * * *